United States Patent
Sun et al.

(10) Patent No.: US 6,313,638 B1
(45) Date of Patent: Nov. 6, 2001

(54) DUAL-CHANNEL PHOTO-IONIZATION DETECTOR THAT ELIMINATES THE EFFECT OF ULTRAVIOLET INTENSITY ON CONCENTRATION MEASUREMENTS

(75) Inventors: Hong T. Sun, Sunnyvale; Peter C. Hsi, Fremont, both of CA (US)

(73) Assignee: Rae Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/271,612

(22) Filed: Mar. 17, 1999

(51) Int. Cl.$^7$ .................................................... G01N 27/62
(52) U.S. Cl. .............................................................. 324/464
(58) Field of Search .................................... 324/464, 468; 313/494

(56) References Cited

U.S. PATENT DOCUMENTS

| | | | |
|---|---|---|---|
| 5,528,150 | * 6/1996 | Sterns et al. | 324/464 |
| 5,561,344 | * 10/1996 | Hsi | 313/494 |
| 6,023,169 | * 2/2000 | Budovich et al. | 324/464 |

* cited by examiner

Primary Examiner—Safet Metjahic
Assistant Examiner—James C Kerveros (57) ABSTRACT

A dual-channel photo-ionization detector (PID) and a method for calculating the gas concentration in the PID are disclosed. The PID includes a UV light source which produces a UV light to ionize a gas, first and second identical ion detectors for measuring first and second currents including ion, and a UV shield which differentially shields the ion detectors from the UV light. The differential shielding of the ion detectors enables the PID to differentiate between current caused by ions and current caused by the photoelectric effect of the UV light. The detector measures a concentration of the gas irrespective of a variation of an intensity of the UV light. A heater in the PID stabilizes the temperature for measurements and prevents condensation in the PID. The method includes: shielding the first ion detector from the UV light and exposing the second ion detector to the UV light; and deciding the concentration of the ionizable gases independent of an intensity of the UV light by comparing the first and second currents. In addition, the calculation of the gas concentration independent of the UV light intensity and a self-cleaning capability of the PID promote a construction of an integrated PID sensor module which is sealed to prevent a user from opening the sensor module. The sensor module, including the UV light source, the ion sensors and the UV shield in a single housing, easily plugs into the socket in a structure including the remainder PID.

34 Claims, 6 Drawing Sheets

DUAL-CHANNEL PHOTO-IONIZATION DETECTOR THAT ELIMINATES THE EFFECT OF ULTRAVIOLET INTENSITY ON CONCENTRATION MEASUREMENTS

BACKGROUND

1. Field of the Invention

This invention relates to a volatile gas detector and particularly to a portable photo-ionization detector (PID).

2. Description of Related Art

Figure 1:
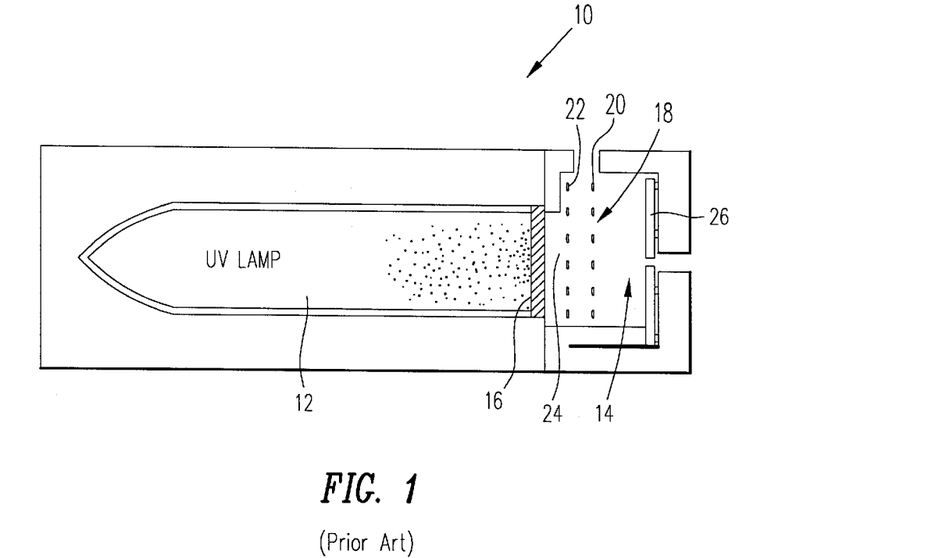
FIG. 1 is a block diagram of a known photo-ionization detector (PID)

FIG. 1 illustrates a known photo-ionization detector (PID) 10 for detecting volatile gases. PID 10 includes an ultraviolet (UV) lamp 12, an ion detector 18 and a UV monitor 26. In operation , UV lamp 12 produces high-energy photons having energy above 9.2 electron volt (eV) which emanate through an optical window 16 into an ionization chamber 14. In ionization chamber 14, the UV photons collide with gas molecules including volatile gas having ionization potentials below the energy of the UV photons. This ionizes the volatile gas molecules, creating detectable ions and electrons.

Ion detector 18 includes a negative electrode 20 and a positive electrode 22 which have a high voltage difference (e.g., greater than 150 V). Accordingly, negative electrode 20 attracts positively charged particles such as ions, and positive electrode 22 attracts negatively charged particles such as electrons. As a result, the production of volatile gas ions causes a current from electrode 22 to electrode 20 that depends on the number of ions produced. The concentration of the volatile gases in ionization chamber 14 can be determined by measuring the current and the intensity of UV light. At a constant UV light intensity, the measured current is nearly proportional to the volatile gas concentration, and the measured current can be simply converted to the concentration, in parts per million (ppm), of the volatile gases.

PID 10 has a space 24 between optical window 16 and positive electrode 22. Space 24 is a "dead zone" in which positive ions can be trapped. The positive polarity of electrode 22 prevents positive ions in space 24 from reaching electrode 20. Accordingly, the configuration of electrodes 20 and 22 with dead space 24 inhibits the collection of ions and can reduce the range and sensitivity of PID 10. For example, PID 10 typically has a detection range of about 2,000 ppm of ionizable gases.

As mentioned above, the measured current can be simply converted to a concentration of volatile gases if the UV intensity from lamp 12 remains constant. However, the UV intensity typically diminishes during a normal operation of PID 10 due to a variety of factors, including degradation of UV lamp 12, contamination of optical window 16 and the presence of interfering substances such as methane, carbon monoxide or water which block or absorb the UV photons in ionization chamber 14. UV monitor 26, which includes a negatively biased electrode, measures the intensity of the UV light by measuring a current caused by the photoelectric effect of the UV light. In particular, when struck by the UV photons, UV monitor 26 releases electrons which cause a monitor current indicative of the intensity of the UV light. The monitor current can be measured to determine UV intensity variations when calculating the volatile gas concentration. The monitor current can also be used when adjusting the intensity of UV lamp 12, for example, by increasing a supply voltage to lamp 12 in response to the monitor current indicating a low UV intensity. However, the presence of ionizable gases around UV monitor 26 increases the monitor current because a positive electrode of UV monitor 26 also collects positive ions. Accordingly, the monitor current inaccurately measures the UV intensity. Absorption of the UV light along the path from UV lamp 12 to UV monitor 26 further reduces the accuracy of the monitor current as an indicator of the UV intensity. Therefore, a PID that can accurately measure the UV intensity, is needed.

SUMMARY

In accordance with an embodiment of the present invention, a dual-channel photo-ionization detector (PID) includes a UV light source, a first ion detector that measures a first current primarily resulting from the ionized gases, a second ion detector that measures a second current resulting from the ionized gases and photoelectric emission of electrons. A UV shield blocks the UV light so that the first ion detector is exposed to less UV light than is the second ion detector. The ion detectors are otherwise structurally identical and symmetric in relation to the UV source. The differential shielding of the ion detectors enables the PID to separate the UV light intensity dependency from the measurement of the concentration of the ionizable gas irrespective of variations in the UV light intensity. Embodiments of the PID can determine the ionizable gas concentration accurately to a ppb (parts per billion) level without frequent calibrations of the UV light intensity.

In accordance with another aspect of the invention, a PID includes a heater that maintains the temperature inside the ionization chamber to prevent condensation and stabilize parameters affecting concentration measurements. With the heater, operation of the PID in a humid environment does not cause condensation inside the ionization chamber. Further, the heater reduces thermal variations which might affect measurements. Accordingly, the PID with a heater can provide better accuracy of volatile gas concentration measurements in a wider variety of environments.

The determination of the gas concentration being independent of the UV light intensity and a self-cleaning capability of the PID eliminate the need for manual cleaning of the UV light source or the ionization chamber and allow integration of a PID sensor module including a UV lamp and an ionization chamber with detector electrodes enclosed. The module can be sealed to prevent disassembly for cleaning. Accordingly, delicate components in the sealed sensor module are less subject to damage. Further, the module positions and configures its components for optimal performance and reduces the need for calibrations since the configuration is fixed and not changed by disassembly, cleaning, or reassembly. The module as a unit can be plugged to the PID having other parts for operating the sensor module.

In one embodiment of the sensor module, a single housing of the sensor module includes the UV light source, the electrodes for the ion detectors, and the UV shield. The sensor module may further include a heater.

Another aspect of the invention provides a method for calculating the gas concentration in the above-described PID. The method includes: shielding the first ion detector from the UV light; exposing the second ion detector to the UV light; measuring a first and second currents with a first reference gas having a known concentration in the PID; and measuring a first and second currents with a second reference gas having a known concentration in the PID. The currents measured at the first and second ion detectors can be modeled as functions of a concentration of the ionizable gases and an intensity of the UV light. Since the two ion detectors are identical except for their exposures to the UV light, the difference between the first and second currents is due solely to the UV light intensity. Parameters for the models of the currents can be determined from the current measurements with the reference gases, and the concentration of ionizable gases can be calculated irrespective of the UV light intensity.

BRIEF DESCRIPTION OF THE DRAWINGS

Use of the same reference symbols in different figures indicates similar or identical items.

DETAILED DESCRIPTION OF THE PREFERRED EMBODIMENTS

A dual-channel photo-ionization detector (PID) includes two sensors (e.g., ion detectors) that are identical except for exposure of their electrodes to UV light. In an exemplary embodiment, a UV shield exposes the electrodes of a first sensor to direct UV light and protects the electrodes of a second sensor from direct UV light exposure. Accordingly, the second sensor measures a current which is predominantly due to ionized volatile gas. The first sensor measures a current which includes a first component caused by ionized gas and a second component caused by UV light liberating electrons from the electrodes of the first sensor. Since the two sensors are identical other than UV exposure of electrodes, the first component of the current that the first sensor measures is same as the current that the second sensor measures. The difference between the measurements of the two sensors is due to the photoelectric effect and indicates the UV intensity at the location of the sensors. Accordingly, UV intensity can be accurately eliminated from the determination of gas concentration.

Figure 2:
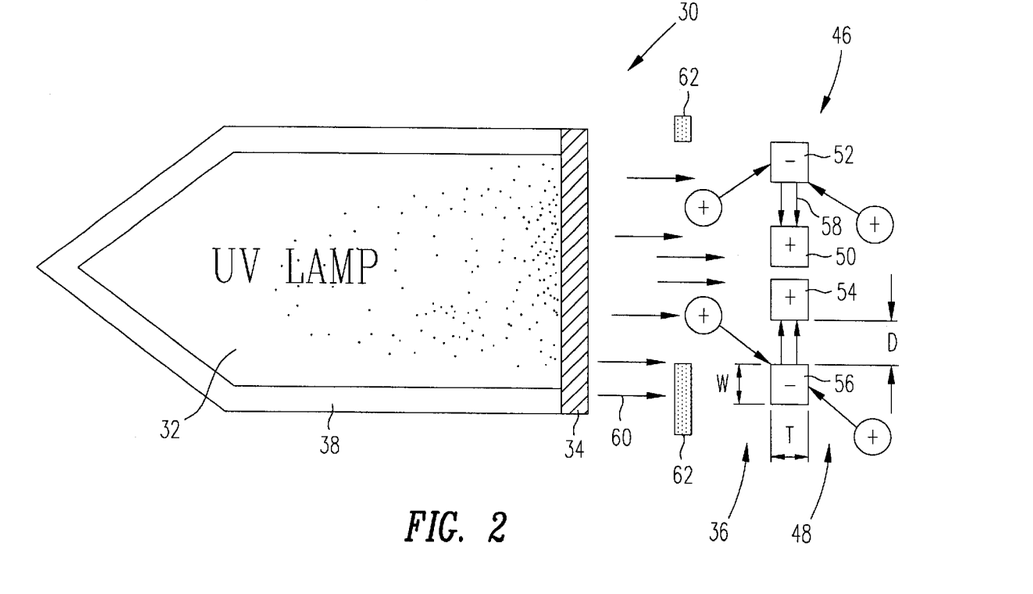
FIG. 2 is a schematic cross sectional view of a portion of a PID having two ion detectors in accordance with an embodiment of the present invention.

FIG. 2 shows a dual-channel PID 30 in accordance with an embodiment of the present invention. PID 30 includes a UV lamp 32 that radiates UV photons or UV light 60 (light having a wavelength less than about 150 nm) through an optical window 34 into an ionization chamber 36. UV lamp 32 includes a sealed envelope 38, preferably manufactured of glass. Envelope 38 contains a mixture of inert gases, such as helium (e.g., 40%), argon (e.g., 30%) and krypton (e.g., 30%) at a reduced pressure (e.g., 25 Torr). Illustrative dimensions for envelope 38 are 0.10–1.00 inch in diameter and 0.20–2.00 inch in length. Optical window 34, which is made of a single crystal material, is disposed at an end of envelope 38. For example, optical window 34 may be manufactured of lithium fluoride (LiF), magnesium fluoride ($MgF_2$), calcium fluoride ($CaF_2$) or barium fluoride ($BaF_2$) which transmit UV photons of 11.7 electron volts (eV), 10.6 eV, 9.8 eV, and 9.2 eV, respectively.

Figure 3:
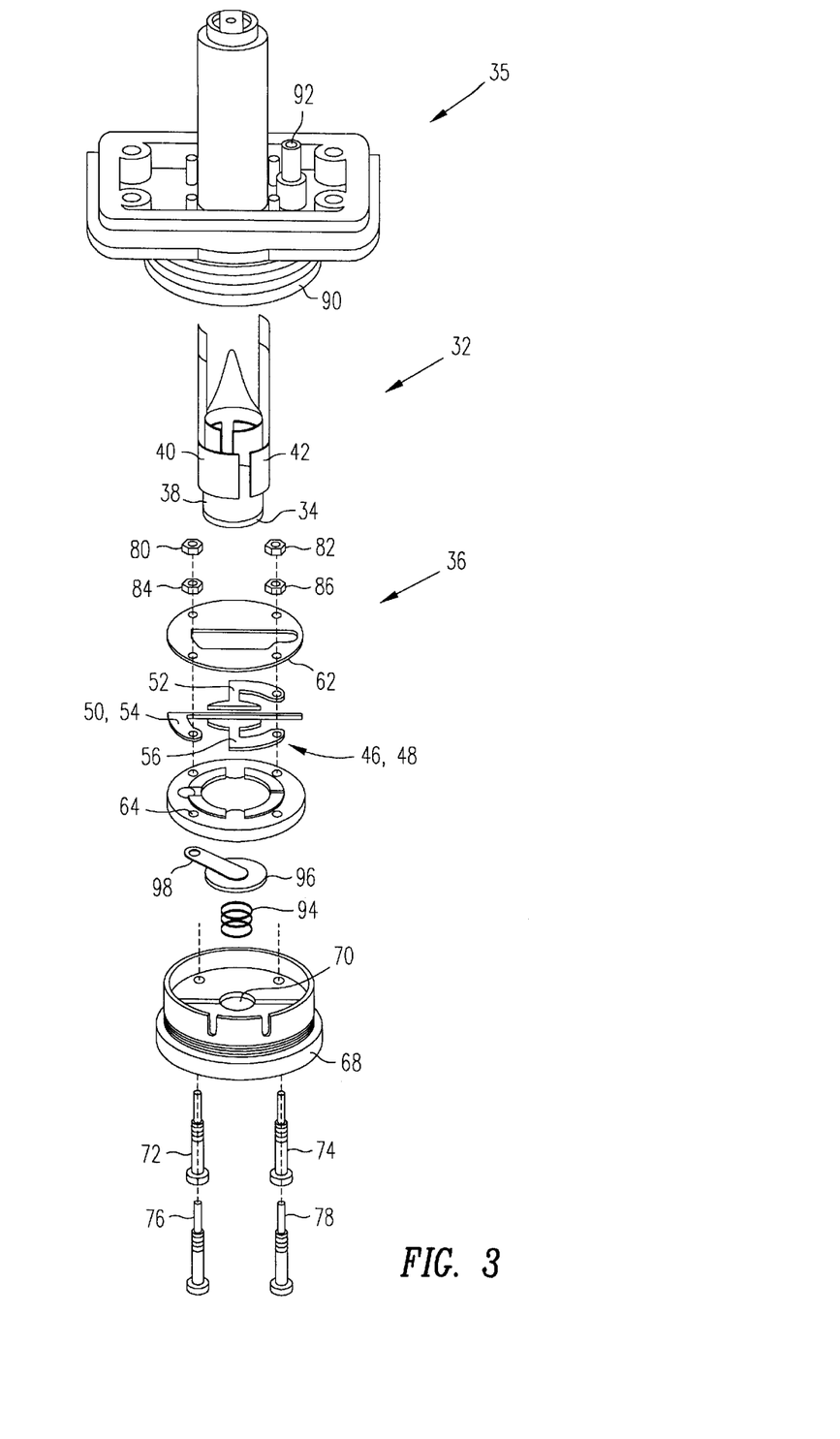
FIG. 3 is an expanded perspective view of a PID gas sensor in accordance with another embodiment of the invention.

FIG. 3 shows a similar dual-channel PID 35, where UV lamp 32 is between two plates or driver electrodes 40 and 42 which connect a lamp driver circuit (not shown) supplying a high voltage AC signal. Driver electrodes 40 and 42 may be manufactured of metal or alloy plates, measuring, for example, 0.20 inches by 0.20 inches. The lamp driver circuit provides to driver electrodes 40 and 42 an AC signal of about 650–1250V at a frequency of about 100 kHz. Consequently, a strong AC electrical field inside envelope 38 ionizes the inert gases creating ions and free electrons. The electrons and the ions inside envelope 38 recombine to generate UV photons in a process known as glow discharge. Depending on the material of choice for optical window 34, UV photons having a desired energy pass through optical window 34. The lamp driver circuit for generating the high voltage AC signal across plates 40 and 42 is described in U.S. Pat. No. 5,773,833 to Hsi, assigned to the assignee of the present invention. U.S. Pat. No. 5,773,833 is hereby incorporated herein by reference in its entirety. A microprocessor (not shown) can adjust the high voltage AC signal that is applied to plates 40 and 42, and thereby adjust the UV intensity of UV lamp 32.

Another energy saving feature of UV lamp 32 is that driver electrodes 40 and 42 are insulated from the ions and the electrons inside envelop 38 during the glow discharge process. Accordingly, no DC current flows between driver electrodes 40 and 42, and initiating and sustaining the glow discharge does not suffer from energy loss due to DC current through the plasma. Miniaturization of UV lamp 32 and envelope 38 also saves power because smaller gas volumes require less energy to initiate and sustain the glow discharge. Envelope 32 is easily miniaturized because UV lamp 32 does not require electrodes or other devices inside envelope 38, and the total power consumed by lamp driver circuit 44 and UV lamp 32 can be less than 100 mW.

Returning to FIG. 2, the UV photons from UV lamp 32 enter ionization chamber 36 and ionize volatile gas molecules inside ionization chamber 36. A first ion detector 46 and a second ion detector 48 are positioned proximal to optical window 34 to collect the resulting electrons and ions. First and second ion detectors 46 and 48 are similar or substantially identical to each other and are in a common plane that is perpendicular to a direction of the UV light. A distance from UV lamp 32 to first ion detector 46 is identical to a distance from UV lamp 32 to second ion detector 48. The only difference between first and second ion detectors 46 and 48 is the degree of shielding from UV light 60, which is discussed below.

First and second ion detectors 46 and 48 respectively include pairs of electrodes; a first bias (positive) electrode 50 and a first measurement (negative) electrode 52 for first ion detector 46, and a second bias (positive) electrode 54 and a second measurement (negative) electrode 56 for second ion detector 48. Electrodes 50, 52, 54 and 56 of ion detectors 46 and 48 can be made of various metals and alloys, preferably stainless steel. Electrodes 50, 52, 54 and 56 can also be formed by depositing a conductive electrode layer on a substrate, masking selected portions of the electrode layer, and etching the remaining portions from the substrate. Instead of the masking and etching, portions of the substrate can be removed so as to form electrodes 50, 52, 54 and 56. Examples of materials used for the electrode layer and the substrate include platinum on a ceramic substrate, copper on a printed circuit board, and gold on a silicon wafer. Illustrative dimensional specifications of electrodes 50, 52, 54 and 56 are about 0.01 to about 0.20 inches in thickness T, most preferably about 0.02 inches in thickness, and about 0.01 to about 0.08 inches in width W, most preferably about 0.02 inches in width. The distance or separation D between bias and measurement electrodes 50 and 52 or 54 and 56 is about 0.01 to about 0.20 inches, most preferably about 0.04 inches. It is understood that these dimensions are illustrative in nature and that electrodes 50, 52, 54 and 56 can have other thicknesses, widths and separations.

Bias electrodes 50 and 54 have a positive bias voltage and repel positive ions formed by photo-ionization. Measurement electrodes 52 and 56 are near ground voltage and separated from bias electrodes 50 and 54 to create an electrical field 58 between bias electrode 50 and measurement electrode 52 and between bias electrode 54 and measurement electrode 56. Measurement electrodes 52 and 56 attract the positive ions. As a result, a first current $S_1$ flows between electrodes 50 and 52, and a second current $S_2$ flows between electrodes 54 and 56. The first and second currents $S_1$ and $S_2$ are used for determination of the volatile gas concentration, as described further below.

As illustrated in FIG. 2, electrical field 58 between electrodes 50 and 52 and between electrodes 54 and 56 is perpendicular to the direction of propagation of UV light 60. The perpendicular relationship allows ion detectors 46 and 48 to be more sensitive to the ionizable gases and thus promotes an accurate and sensitive measurement of the ionizable gas concentration. As disclosed in U.S. patent application Ser. No. 09/177,669, filed Oct. 22, 1998, entitled "A PHOTO-IONIZATION DETECTOR FOR VOLATILE GAS MEASUREMENT AND A METHOD FOR SELF-CLEANING", which is herein incorporated by reference in its entirety, ion detects such as ion detectors 46 and 48 can accurately measure gas concentrations up to about 10,000 ppm of ionizable gases.

The number of ions formed and detected depends on the volatile gas concentration and the intensity of the UV light from the UV lamp. Thus, the known PID of FIG. 1 includes a UV monitor 26 to measure the UV light intensity for a use in determining the ionizable gas concentration. However, various factors can prevent an accurate measurement of the UV light intensity in the PID of FIG. 1. Among the factors is the absorption of UV light along the long traveling distance to the UV monitor 26.

PID 30 includes a UV shield 62 between optical window 34 and ion detectors 46 and 48 that shields measurement electrode 56 of ion detector 48 from UV light 60. During an operation of PID 30, UV light 60 striking ion detectors 46 and 48 can liberate electrons from electrodes 50, 52 and 54. Electrons liberated from bias electrodes 50 and 54 are, in general, attracted back to positive bias electrodes 50 and 54 and do not contribute to a base line current (i.e., a current presented even in the absence of ionizable gases) in respective ion detectors 46 and 48. However, bias electrodes 50 and 54 can capture electrons liberated from measurement electrodes 52 and 56 which lead to a base line current. UV shield 62, which is preferably made of a polytetrafluoroethene (Teflon) sheet, is between optical window 34 and measurement electrode 56 and stops UV light 60 from striking measurement electrode 56. Even though, as shown in FIG. 2, this embodiment completely shields measurement electrode 56 from UV light 60 and completely exposes measurement electrode 52, another embodiment allows UV light 60 to strike electrodes 52 and 56 at different degrees. In other words, UV shield 62 differentially exposes electrodes 52 and 56 to UV light 60. Alternatively, a layer of material (not shown) which is inert to the gases and ions generated in ionization chamber 36, has an electrical insulation property, and is opaque to high energy UV light may be employed as a UV shield on electrode 56. For example, a photo-resist polymer made of polytetrafluoroethene (Teflon) or a ceramic layer made of alumina may be formed on a surface of measurement electrode 56 facing optical window 34 to serve as a UV shield. The UV shield as just described may also be employed for bias electrodes 50 and 54.

FIG. 3 shows an expanded perspective drawing of components in an exemplary embodiment of PID 35. By way of illustration and not limitation, PID 35 of the present invention measures 2.50 inches in length by 1.75 inches in width by 3.00 inches in height, and weighs 60 g. UV lamp 32, including optical window 34, glass envelope 38, and driver electrodes 40 and 42 are contained in a lamp housing 90. Bias and measurement electrodes 50, 52, 54 and 56 of ion detectors 46 and 48 are parallel to each other in a common plane and disposed between UV shield 62 and an insulating spacer 64. In this embodiment, ion detectors 46 and 48 share a common electrode for bias electrodes 50 and 54, which is described below with reference to FIG. 4. An insulation spacer 64 has bumps to improve the alignment of ion detectors 46 and 48 by fitting electrodes 50, 52, 54 and 56 between the bumps. UV shield 62 only keeps from UV light 60 from measurement electrode 52. In this embodiment, openings in UV shield 62, electrodes 50, 52, 54 and 56, and insulating spacer 64 form ionization chamber 36 with a free volume of about 5 micro-liters.

Bias electrodes 50 and 54 connect to bias circuits (not shown) via pins 72 and 76 and nuts 80 and 84, and measurement electrodes 52 and 56 are at near ground potential and connect to two current measurement circuits (not shown) via pins 74 and 78 and nuts 82 and 86. An end cap unit 68 encloses ionization chamber 36 within lamp housing 90. End cap unit 68 has a gas inlet 70, and lamp housing 90 has a gas outlet 92 for a pump or a fan that circulates the gases through ionization chamber 36. Driver electrodes 40 and 42, bias and measurement electrodes 50, 52, 54 and 56, connecting pins 72, 74, 76 and 78, and connecting nuts 80, 82, 84 and 86 are made of conductive materials including metals and alloys. A preferable material is stainless steel. UV shield 62 and insulating spacer 64 may be manufactured from an inert material sheet, Teflon, having a thickness of about 0.02 inches and a diameter of about 1.50 inches. End cap 68 and lamp housing 90 are also machined from materials that are inert to volatile gases and opaque to the high-energy UV light. These materials include acrylonitril butadiene styrene, polycarbonate, polyethelyne, polypropylene, polyurethane, polyvinyl chloride, and polytetrafluoroethene (Teflon).

PID 35 further includes a heater 96 which is between insulating spacer 64 and end cap 68. Heater 96 has a positive heater electrode 98 and a spring ground electrode 94. Positive heater electrode 98 and spring ground electrode 94 drive heater 96. In FIG. 3, heater 96 is a positive temperature coefficient (PTC) thermistor, such as Digi-Key PTC thermistor (Part Number: KC003P-ND). Alternatively, heater 96 can be a solid-state heater, a filament heater, a heating tape, a radiated heater, or any heater with a heating element and a thermostat. Generally, heater 96 maintains the ionization chamber of PID 35 at a nearly constant temperature and prevents condensation of entering gas. In a normal operation, heater 96 heats ionization chamber 36 up to about 300° C., but any temperature (e.g., 40 to 50° C.) that is above the temperature of the gas entering PID 35 is sufficient to prevent condensation. In the absence of heater 96, when PID 35 is cooler than the ambient air, moistures can condense on optical window 34 and electrodes 50, 52, 54 and 56. The condensation on optical window 34 blocks UV light 60, and the condensation on electrodes 50, 52, 54 and 56 can block UV light and cause a leakage current between electrodes 50, 52, 54 and 56. Heater 96 heats optical window 34 and electrodes 50, 52, 54 and 56 in ionization chamber 36 to prevent condensation. In addition, heater 96 can maintain PID 35 at an optimal or constant operating temperature and stabilizes the baseline or zero signal of PID 35 for a ppb level of accuracy.

Figure 4:
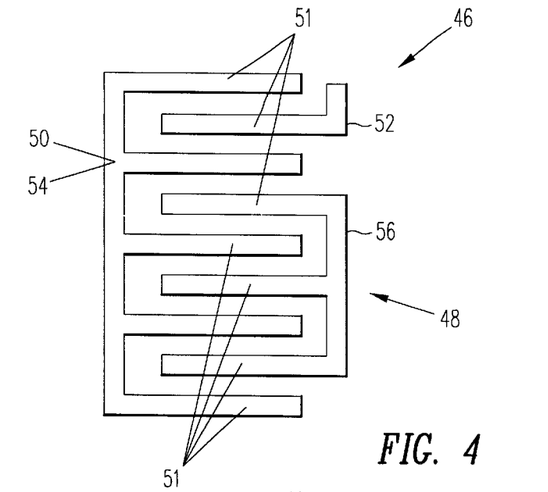
FIG. 4 is a plan view of electrodes for two ion detectors, having a common bias electrode and separate signal electrodes.
Figure 5:
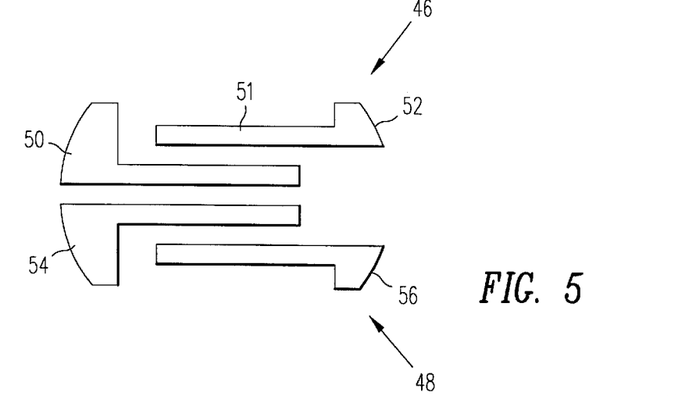
FIG. 5 is a plan view of electrodes for two ion detectors, having separate bias and signal electrodes.
Figure 6:
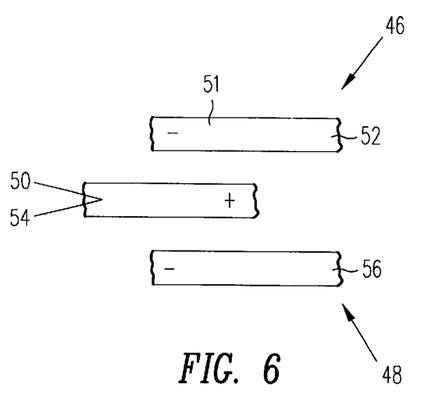
FIG. 6 is a partial view of electrodes for two ion detectors, having straight electrodes.
Figure 7:
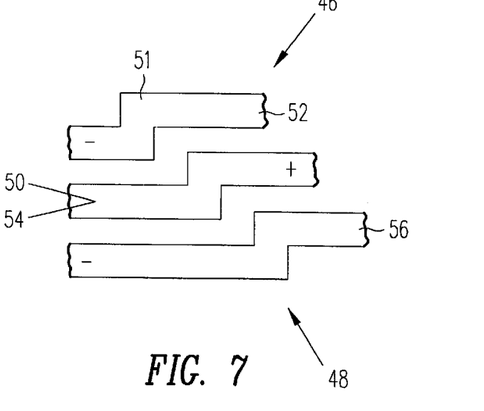
FIG. 7 is a partial view of electrodes for two ion detectors, having step-like electrodes.

Bias and measurement electrodes 50, 52, 54 and 56 of ion detectors 46 and 48 can have a variety of shapes. FIGS. 4 to 7 show examples of electrode configurations. Bias electrodes 50 and 54 can be combined as shown in FIG. 4 or separated as shown in FIG. 5. Each of bias and measurement electrodes 50, 52, 54 and 56 has at least one digit 51, and digits 51 are typically positioned in parallel. In FIG. 4, measurement electrode 52 of ion detector 46 has a single digit, and measurement electrode 56 of ion detector 48 has three digits. Accordingly, under the same conditions ion detector 48 measures a current that is about three times the current that ion detector 46 measures. This type of proportionality in the currents may equalize noise or statistical error in measurements when ion detector 46 measures current including gas ions and photoelectrons and ion detector 48 measures gas ions. Digits 51 of bias and measurement electrodes 50, 52, 54 and 56 can be linear or straight, as illustrated in FIG. 6, or non-linear, as in FIG. 7. FIG. 7 illustrates digits 51 having a "step-like" shape, but digits 51 may have other patterns or shapes. Further, each of bias and measurement electrodes 50, 52, 54 and 56 can have one or more digits 51.

Figure 8A:
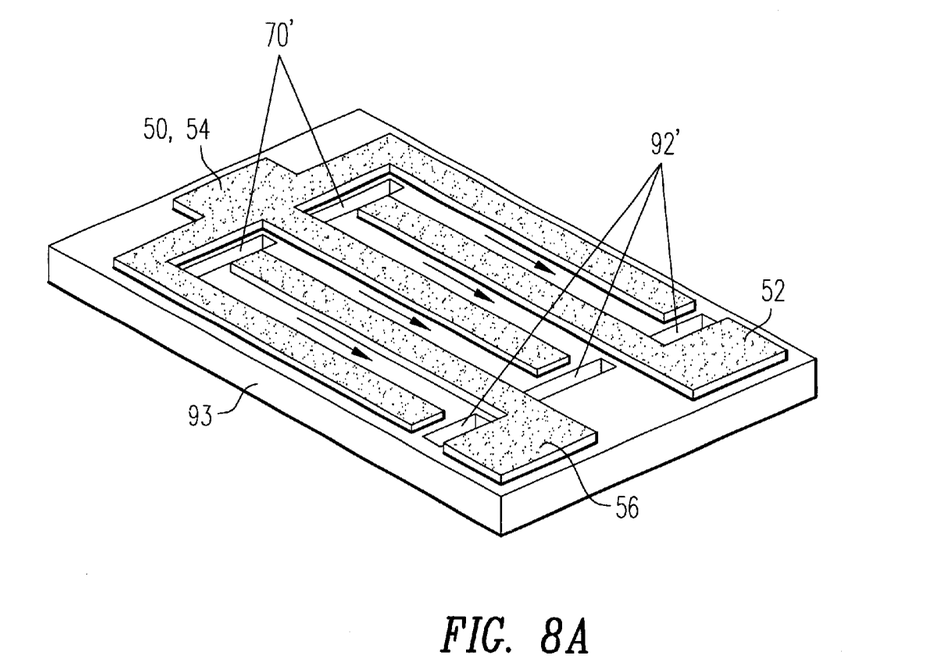
FIGS. 8A and 8B are respectively a perspective top view and a perspective bottom view of an integrated structure including electrodes and a heater.
Figure 8B:
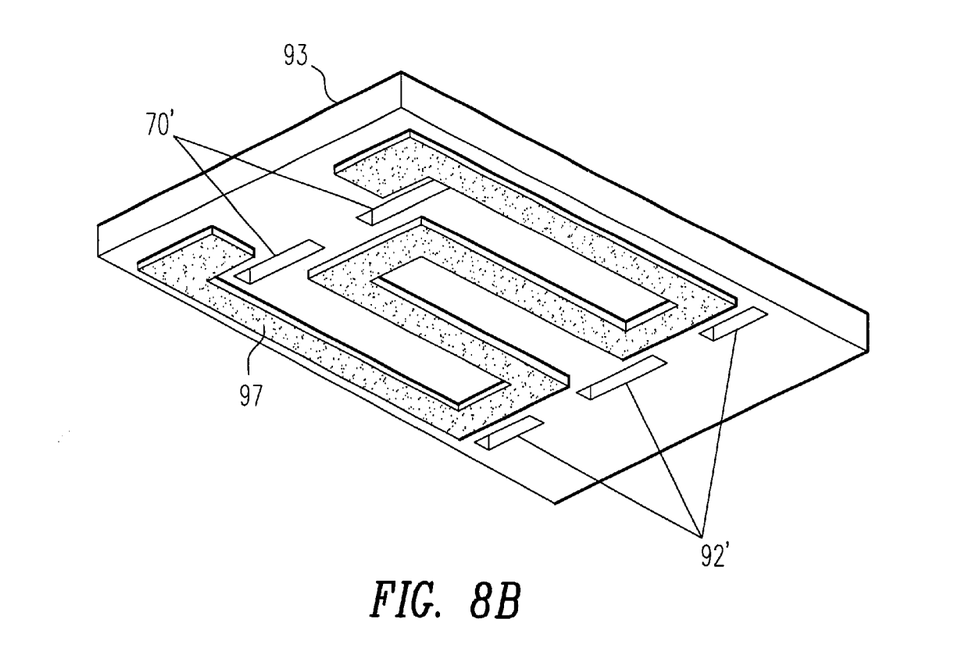

Another aspect of the present invention allows integration of a heater and the electrodes of ion detectors. FIGS. 8A and 8B show an integrated structure including the electrodes of ion detectors 46 and 48 and a film heater 92 on a substrate 93. Substrate 93 can be, for example, a ceramic substrate, a printed circuit board, or a silicon substrate. Conductive layer deposition and patterning form electrodes 50, 52, 54 and 56 on the top surface of substrate 93 and heater 92 on the bottom surface of substrate. Exemplary material combinations of electrodes 50, 52, 54 and 56 (or heater 92) and substrate 93 are platinum on a ceramic substrate, copper on a printed circuit board, and gold on a silicon substrate. As a UV-shield, a coating layer can be formed only on specific areas of measurement electrodes 52 and 56 or at different levels of coverage. Substrate 93 further includes gas inlet holes 70' and gas outlet holes 92'. Holes 70' and 92 are respectively aligned to inlet 70 and outlet 92 of the PID of FIG. 3 so that gas flows in the direction shown in FIG. 8A.

In accordance with a further aspect of the invention, a sensor module includes an ionization chamber, a UV lamp, two ion detectors and a gas path in a single integrated or tamper-resistant sensor housing. The sensor module plugs into a PID including a power supply, a gas pump or fan, control and processing circuits, and other parts for operating the sensor module. This "plug and play" type PID sensor module provides an advantage over conventional PID sensors that allow or require users to disassemble PID sensors to clean components. (The conventional PID sensor requires the user to clean components of the sensor, particularly the UV lamp.) Cleaning and reassembling the sensor can damage delicate components, change the orientation or configuration of critical component, and decrease the sensitivity of the sensor. Further, calibration of the PID may be required after cleaning.

Several features of the PIDs described herein enable construction of a sensor module that a user does not need to disassemble. One feature that allows sealing of the sensor module is self-cleaning of the ionization chamber. Referring to FIG. 1, during a normal operation of conventional PID 10, the effectiveness of the PID diminishes due to the build-up of contamination in lamp 12 and ionization chamber 14, including on electrodes 20 and 22 of ion detector 18. Typically, the contamination includes a coating of metal atoms, oil film, dust particles, or other polymer-like coating substances. The build-up of such contamination on the surface of optical window 16 decreases the available UV light intensity in ionization chamber 14. As a result, a user must often clean ionization chamber 14, including optical window 16. The present invention provides a method for self-cleaning a ionization chamber. In particular, circulation of air through the ionization chamber is stopped while the UV lamp 32 remains on. The UV light creates ozone in the ionization chamber which oxidizes and removes residue built up in the ionization chamber. The method is further described in the above-incorporated U.S. patent application Ser. No. 09/177,669.

In addition to the self-cleaning capability, the use of dual channel ion detectors can extend the time between required cleanings because, as will be described with reference to FIG. 10, the gas concentration can be measured accurately even at low UV light intensities at which a single channel ion detector cannot accurately measure a gas concentration.

Figure 9:
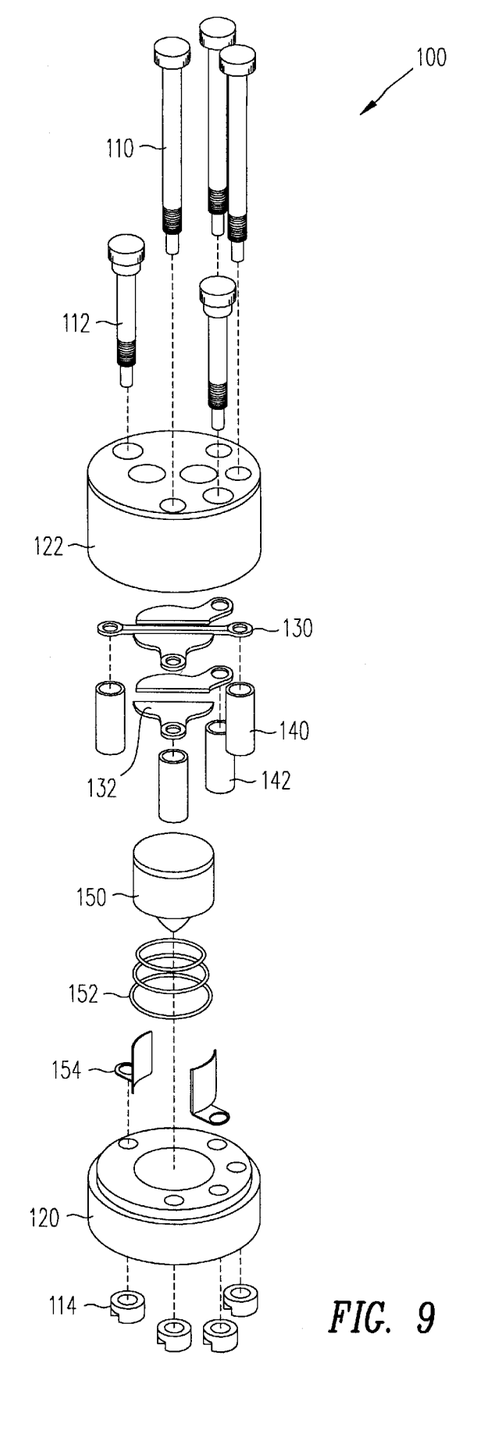
FIG. 9 is an expanded perspective view of a tamper-resistant PID gas sensor module in accordance with another embodiment of the invention.

FIG. 9 shows an example of an integrated sensor module 100. Sensor module 100 is similar to the structure shown in FIG. 3. Sensor module 100 includes a UV lamp 150, lamp electrodes 154 which drive UV lamp 150, a UV shield 132, spacers 142, sensor electrodes 130 for two ion detectors, and spacers 140 in a housing 120 covered with a housing cover 122. Spacers 140 and 142 decide respective positions of sensor electrodes 130 and UV shield 132 in an ionization chamber formed within housing 120. Sensor module 100 further includes sensor pins 110, lamp pins 112 and nuts 114 to seal housing 120 and housing cover 122. An optional heater (not shown) such as heater 96 (FIG. 3) can also be included adjacent to electrodes 130. Integrated module 100 plugs into a PID body (not shown) with sensor and lamp pins 110 and 112 making electrical contact with circuitry in the PID body. Sensor pins 110 are an electrical communication medium between the PID body and sensor electrodes 130, and lamp pins 112 are a communication medium between the PID body and lamp electrode 154. Pins 110 and 112 also seal sensor module 100 in a manner that makes disassembly of sensor module 100 difficult, so that sensor module 100 is not designed to permit user access to UV lamp 150 or sensor electrodes 130. Sensor module 100 enables factory setting and optimal configuration of UV lamp 150 and gas path and prevents users from opening sensor module 100 and damaging sensor electrodes 130 and/or UV lamp 150.

Figure 10:
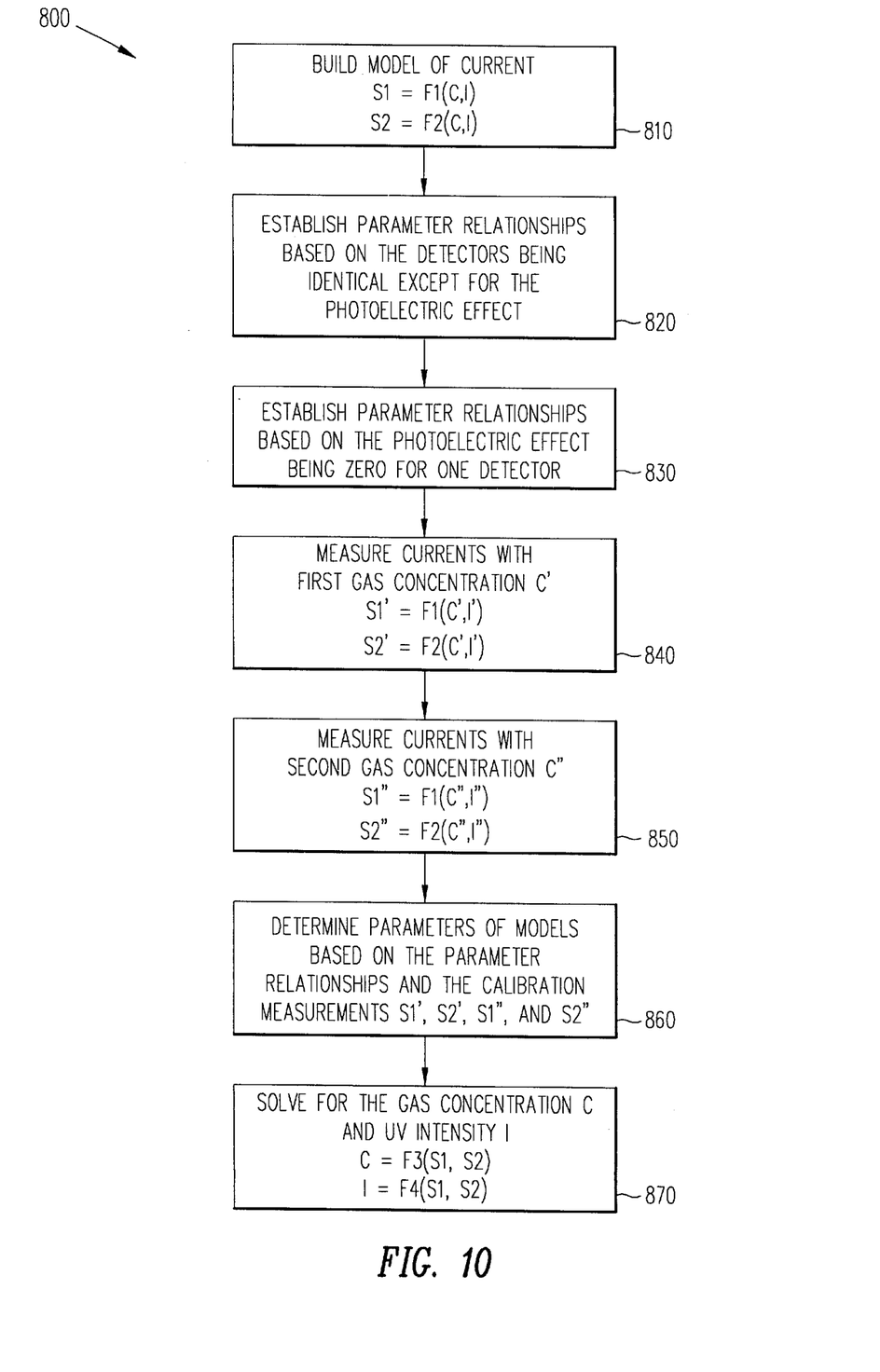
FIG. 10 is a flowchart of a process for measuring a gas concentration and UV intensity in accordance with an embodiment of the present invention.

FIG. 10 is a flowchart of a method 800 for a simultaneous determination of an ionizable gas concentration C and a UV light intensity I based on the dual channel currents $S_1$ and $S_2$ measured by ion detectors 46 and 48 of PID 30. Each of ion detectors 46 and 48 may have a separate current measurement circuit or amp meter, or a single current measurement circuit (not shown) can consecutively measure the currents through ion detectors 46 and 48. Alternatively, ion detectors 46 and 48 may have a differential measurement circuit (not shown) that measures the difference $S_2$–$S_1$ between the current $S_1$ through ion detector 46 and the current $S_2$ through ion detector 48.

Method 800 begins in step 810 with modeling of two current signals $S_1$ and $S_2$ as functions of a gas concentration, C, and a UV light intensity, I; $S_1 = F_1(C,I)$, and $S_2 = F_2(C,I)$. Signal $S_1$ is the current that ion detector 46 detects, and signal $S_2$ is the current that ion detector 48 detects. The two functions $F_1$ and $F_2$ can be linear or non-linear. Steps 820 and 830 respectively use the similarity of ion detectors 46 and 48 and the elimination of the photoelectric current from detector 48 to determine relationships between the parameters of the model $F_1$ and $F_2$. For calibration purposes, signals $S_1'$ and $S_2'$ are measured at a known gas concentration C' (step 840), and signals $S_1''$ and $S_2''$ are measured at another known gas concentration C'', (step 850). The UV intensities I' and I'' during calibration steps 840 and 850 should be about equal if the calibration steps 840 and 850 are consecutive. Then, step 860 determines the parameters of functions $F_1$ and $F_2$ from the calibrated measurements $S_1'$, $S_2'$, $S_1''$, and $S_2''$. Gas concentration C and UV light intensity I are then determined as functions $F_3(S_1, S_2)$ and $F_4(S_1, S_2)$ of two currents $S_1$ and $S_2$ in step 870. The concentration of ionizable gases C and UV light intensity I are determined by measuring $S_1$ and $S_2$ and using the measurements in functions $F_3$ and $F_4$.

An exemplary approach for calculating gas concentration C and UV light intensity I is described below. With this approach, the currents $S_1$ and $S_2$ are presumed to have two contributions. An ionized gas contribution is proportional to the product of the gas concentration C and the UV light intensity I. A photoelectric effect contribution is proportional to the UV intensity I. Thus, equations (1) and (2) describe current signals $S_1$ and $S_2$ through ion detectors 46 and 48.

$$S_1 = a_1 IC + b_1 I \quad (1)$$

$$S_2 = a_2 IC + b_2 I \quad (2)$$

In equations (1) and (2), $a_1$, $b_1$, $a_2$ and $b_2$ are parameters to be determined by calibrations; one at a known gas concentration C' under a UV light intensity I', the other at a known gas concentration C'' under a UV light intensity I''. Since both ion detectors 46 and 48 are at the same distance from UV lamp 32, UV light intensity I in equations (1) and (2) is the same for both detectors 46 and 48 and for both signals $S_1$ and $S_2$. Equations (3) to (6) are from the calibration measurements $S_1'$, $S_2'$, $S_1''$, and $S_2''$.

$$S_1' = a_1 I'C' + b_1 I' \quad (3)$$

$$S_2' = a_2 I'C' + b_2 I' \quad (4)$$

$$S_1'' = a_1 I''C'' + b_1 I'' \quad (5)$$

$$S_2'' = a_2 I''C'' + b_2 I'' \quad (6)$$

since the two ion detectors are identical and ion detector 48, which produces $S_2$, is completely shielded from the UV light, we have:

$$a_1 = a_2 \quad (7)$$

$$b_2 = 0 \quad (8)$$

Based on the calibration data $S_1'$, $S_2'$, C', $S_1''$, $S_2''$, and C'', four constants ($a_1$, $b_1$, $a_2$, and $b_2$) and two variables (I', I'')can be determined from equations (3) to (8).

Once constants $a_1$, $a_2$, $b_1$, and $b_2$ are known, gas concentration C and UV intensity I can be calculated from equations (1) and (2) by substituting the values for the four parameters and measured current signals $S_1$ and $S_2$. Typically, zero air C'=0 and a span gas C''≠0 are used for two-point calibration. For zero air, $S_1' \neq 0$ and $S_2' = 0$. During the calibration, there is almost no change in the intensity of UV light, i.e., I'=I''. In this case, the formula of the gas concentration C becomes:

$$C = \left(\frac{S2}{S2''}\right)\left(\frac{S1'' - S2''}{S1 - S2}\right)C'' \quad (9)$$

where C'' stands for the concentration of the span gas.

The current signals $S_1$ and $S_2$ that the ion detectors of the dual-channel PID measure are proportional to the UV light intensity. Many factors, such as some quenching molecules of methane, carbon dioxide and water that absorb UV light, the degradation and contamination of the UV lamp, changes in ambient conditions including pressure and chemical composition, and flow-rate fluctuation can affect the UV intensity at the ion detectors. In accordance with the invention, the dual-channel PID can read an accurate concentration of volatile gases without frequent calibrations. Moreover, accuracy of the dual-channel PID extends to a ppb level because a zero signal (a signal at the zero air) does not drift and is not affected by UV light intensity fluctuation. In a conventional single-channel PID, zero signal is calibrated at an ambient air or an artificial zero gas, both of which usually contain a small amount of UV-ionizable impurities. These impurities cause the calibrated zero to be higher than the theoretical or absolute zero, and a zero signal drift occurs when varied UV light intensities cause different ionization levels of the impurities. That is, UV lamp contamination and UV lamp degradation can cause the zero signal drift. The drift in the zero signal makes identifying a gas concentration level down to or below 1 ppm difficult. The dual channel PID makes the zero signal stable within a few ppb level. A calculated UV light intensity can indicate whether the UV source needs an adjustment or cleaning or is blocked by quenching gases such as methane.

Instead of the method described with reference to FIG. 10, a PID can determine a gas concentration C using a database or table which includes gas concentrations C indexed by values of current signals $S_1$ and $S_2$. Appropriate data bases for a type of PID can be determined during development or at the factory by repeated calibrations of PIDs using different known sample gases. Once the databases are known, calibration of a particular PID identifies which data base the PID should use. For a measurement, measured current signals $S_1$ and $S_2$ identify one or more nearest points in the data base. When signals $S_1$ and $S_2$ are between index values of the database, interpolation between the points of the data base provides the gas concentration C. If desired, the UV light intensity I can be determined using similar data bases.

Although the invention has been described with reference to particular embodiments, the description is only an example of the inventor's application and should not be taken as a limitation. In particular, even though much of preceding discussion was aimed at dual-channel detectors when both channels use identical ion detectors, alternative embodiments of this invention include dual-channel PID where the ion detectors for the channels are not identical but are disposed at the same distance from the UV light source. Being at the same distance from the source simplifies determination of the concentration because both ion detectors experience the same UV intensity. Additionally, the two ion detectors may have similar configurations but different sizes so that one ion detector collects a proportionally larger current. The proportionality of the currents simplifies removal errors in concentration measurements that intensity variations can cause in prior PIDs. Various other adaptations and combinations of features of the embodiments disclosed are within the scope of the invention as defined by the following claims.

We claim:

1. A photo-ionization detector comprising:
   a UV light source that produces a UV light which ionizes ionizable gases;
   a first ion detector that measures a first current;
   a second ion detector that measures a second current; and
   a UV shield that blocks the UV light so that exposure of the first ion detector to the UV light differs from exposure of the second ion detector to the UV light, wherein the first ion detector and the second ion detector are positioned so that the UV light intensity that ionizes the ionizable gases is the same at the both ion detectors.

2. The photo-ionization detector of claim 1, wherein the first ion detector comprises a first electrode biased to attract negatively charged particles and a second electrode biased to attract positively charged particles, and the second ion detector comprises a third electrode biased to attract negatively charged particles and a fourth electrode biased to attract positively charged particles.

3. The photo-ionization detector of claim 2, wherein the first and third electrodes are separately biased.

4. The photo-ionization detector of claim 2, wherein the first and third electrodes constitutes one electrode so that the first and third electrodes are commonly biased.

5. The photo-ionization detector of claim 2, wherein the second electrode is shielded from the UV light, and the fourth electrode is exposed to the UV light.

6. The photo-ionization detector of claim 2, wherein the first, second, third and fourth electrodes are positioned in a common plane that is perpendicular to a direction of the UV light.

7. The photo-ionization detector of claim 1, wherein the UV shield is between the UV light source and an electrode of the first ion detector.

8. The photo-ionization detector of claim 1, wherein the UV shield is on a surface of the first ion detector that faces the UV source.

9. The photo-ionization detector of claim 1, wherein the first and second ion detectors are parallel in a common plane that is perpendicular to a direction of the UV light.

10. The photo-ionization detector of claim 1, wherein the first ion detector is shielded from the UV light, and the second ion detector is exposed to the UV light.

11. The photo-ionization detector of claim 10, wherein the first ion detector is otherwise substantially identical to the second ion detector.

12. The photo-ionization detector of claim 1, further comprising a heater that heats the UV light source, the first ion detector, and the second ion detector.

13. A photo-ionization detector comprising:
    an ionization chamber;
    a UV light source that directs UV light into the ionization chamber;
    an ion detector that measures a current including the ions that the UV light produces by ionizing ionizable gases; and
    a heater positioned to heat a portion of the ionization chamber, such that condensation of moisture in the photo-ionization detector is prevented.

14. The photo-ionization detector of claim 13, wherein the heater comprises a positive temperature coefficient thermistor.

15. The photo-ionization detector of claim 13, wherein the heater is one selected from a group consisting of a solid-state heater, a filament heater, a heating tape and a radiated heater.

16. The photo-ionization detector of claim 13, wherein the heater and the ion detector are integrated into a single structure.

17. The photo-ionization detector of claim 16, wherein the structure comprises a substrate, the heater is on a bottom surface of the substrate, and the ion detector is on a top surface of the substrate.

18. The photo-ionization detector of claim 17, wherein the structure further comprises throughholes for gas flow along the detector.

19. The photo-ionization detector of claim 13, wherein the heater heats the ionization chamber to a temperature greater than a temperature of gas entering the photo-ionization detector.

20. An integrated sensor module comprising:
    an ionization chamber through which a gas flows;
    a UV light source which directs UV light into the ionization chamber;
    a sensor electrode which is disposed in the ionization chamber so as to measure a current from the ionized gas;
    a housing which forms an external frame of the sensor module; and
    a plurality of pins which protrude from the housing for transferring signals to and from the sensor module.

21. The integrated sensor module of claim 20, further comprising a first ion detector and a second ion detector, wherein each of the ion detectors measures a current including ions formed in the chamber, and the first ion detector includes the sensor electrode.

22. The integrated sensor module of claim 21, wherein the first ion detector comprises a first electrode biased to attract negatively charged particles and a second electrode biased to attract positively charged particles, and the second ion detector comprises a third electrode biased to attract negatively charged particles and a fourth electrode biased to attract positively charged particles.

23. The integrated sensor module of claim 20, further comprising a UV shield which blocks the UV light in a way that exposes the first ion detector to the UV light at a degree different from a degree that the second ion detector is exposed to the UV light.

24. The integrated sensor module of claim 23, wherein the first ion detector is shielded from the UV light, and the second ion detector is exposed to the UV light.

25. The integrated sensor module of claim 20, wherein the UV source comprises a UV lamp having a driver electrode for driving the UV lamp.

26. The integrated sensor module of claim 20, wherein the sensor module is sealed to prevent opening of the housing for cleaning of the UV light source.

27. The integrated sensor module of claim 20, further comprising a heater for heating at least a portion of the integrated sensor module.

28. The integrated sensor module of claim 20, wherein the pins enable the integrated sensor module to be plugged into a photo-ionization detector body which drives the integrated photo-ionization detector sensor module.

29. The integrated sensor module of claim 20, wherein the integrated detector sensor module is sealed to prevent opening.

30. A method for determining a concentration of ionizable gases in a sample, the method comprising:
   directing UV light from a source into an ionization chamber containing a first ion detector and a second ion detector that are the same distance from the source;
   stopping the UV light from reaching a portion of an electrode in the second ion detector while the UV light reaches a matching electrode in the first ion detector;
   passing the sample through the ionization chamber;
   measuring first and second currents using the first ion detector and the second ion detector, respectively; and
   determining the concentration from the first and second currents.

31. The method of claim 30, wherein the first and second ion detectors are substantially identical.

32. The method of claim 30, wherein determining the concentration comprises:
   modeling the first current and the second current as functions of an ionizable gas concentration and a UV light intensity;
   performing calibration measurements;
   determining parameters of the functions from the calibration measurements;
   determining from the functions, a relationship that gives the concentration, as a function of the first current and the second current and independent of intensity of the UV light; and
   determining the concentration using the relationship and measurements of the first current and the second current.

33. The method of claim 30, wherein determining the concentration comprises using measurements of the first and second currents to identify and a concentration in a data base.

34. The method of claim 30, further comprising heating the ionization chamber to a temperature greater than a surrounding environment.

* * * * *